(12) United States Patent
Eiermann et al.

(10) Patent No.: US 6,531,629 B1
(45) Date of Patent: Mar. 11, 2003

(54) METHOD OF PRODUCING ALKANESULFONIC ACID

(75) Inventors: Matthias Eiermann, Limburgerhof (DE); Christian Tragut, Wachenheim (DE); Klaus Ebel, Lampertheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/831,362

(22) PCT Filed: Nov. 22, 1999

(86) PCT No.: PCT/EP99/08994

§ 371 (c)(1),
(2), (4) Date: May 15, 2001

(87) PCT Pub. No.: WO00/31027

PCT Pub. Date: Jun. 2, 2000

(30) Foreign Application Priority Data

Nov. 25, 1998 (DE) .......................................... 198 54 428

(51) Int. Cl.⁷ ............................................. C07C 303/16
(52) U.S. Cl. ...................................................... 562/118
(58) Field of Search .......................................... 562/118

(56) References Cited

U.S. PATENT DOCUMENTS 2,697,722 A   12/1954   Johnson et al.
2,727,920 A   12/1955   Johnson et al.

FOREIGN PATENT DOCUMENTS

WO   WO 98/34914   8/1998

*Primary Examiner*—Paul J. Killos
(74) *Attorney, Agent, or Firm*—Oblon, Spivak, McClelland, Maier & Neustadt, P.C.

(57) ABSTRACT

The invention relates to a process for the prepartaion of alkanesulfonic acids, comprising the following steps:

Figure 1:
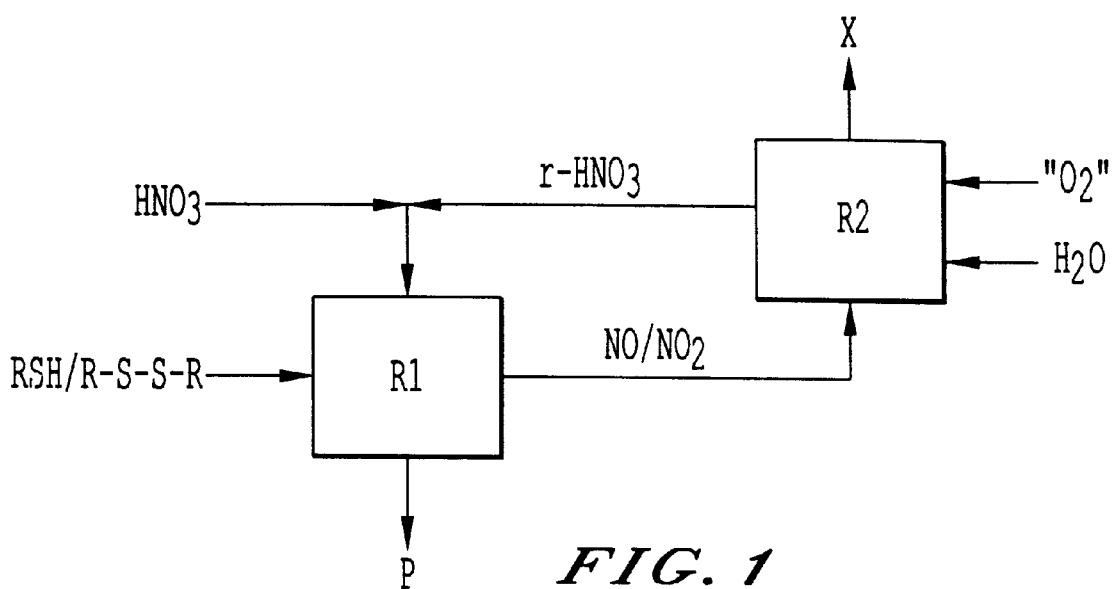

(a) oxidation of alkylmercaptans and/or dialkyl disulfides and/or dialkyl polysulfides having from three to nine sulfur atoms with nitric acid to form alkanesulfonic acids, water, nitrogen oxides and other byproducts, (b) regeneration of the nitrogen oxides obtained from step (a) with oxygen to give nitric acid and recycling of the nitric acid to step (a), where steps (a) and (b) are carried out in reaction chambers separate from one another.

10 Claims, 2 Drawing Sheets

METHOD OF PRODUCING ALKANESULFONIC ACID

The invention relates to a process for the preparation of alkanesulfonic acids.

Alkanesulfonic acids are used in a number of industrial applications. Long-chain alkanesulfonic acids have, for example, surfactant properties, while short-chain alkanesulfonic acids, such as methanesulfonic acid, can, for example, be used as auxilary chemicals for the electrodeposition of noble metals such as tin or lead in the tin plating of printed circuit boards for electronics or in the preparation of tinplate.

The literature describes a number of processes for the preparation of alkanesulfonic acids. For this purpose, alkylmercaptans or dialkyl disulfides, in particular, are used as starting materials, which are usually prepared by the reaction of hydrogen sulfide with alcohols. The oxidation reaction of the alkylmercaptans or of the dialyl disulfides to give the corresponding alkanesulfonic acid can be achieved using a variety of oxidizing agents. For example, the oxidizing agent can be hydrogen peroxide, chlorine, dimethyl sulfoxide or mixtures of dimethyl sulfoxide and hydroiodic acid, and electrochemical oxidation.

WO 98/34914 describes an oxidation of mercaptans and/or dialkyl disulfides using $Br_2$ to give alkanesulfonic acids. The $Br_2$ is preferably obtained from HBr to make handling easier. The oxidation of HBr to $Br_2$ can be carried out with oxygen in the presence of catalytic amounts of nitric acid or with nitric acid itself as oxidizing agent. The nitrogen oxides which form in the oxidation of HBr with nitric acid are reoxidized with oxygen to give nitric acid. In order to avoid over-oxidation of the sulfur compounds present in the process to give sulfuric acid, the oxidation of HBr to $Br_2$ and the oxidation of the mercaptans and/or dialkyl disulfides with $Br_2$ can be carried out in separate reactors.

Another method of preparing alkanesulfonic acids is the oxidation of alkylmercaptans or dialkyl disulfides with oxygen in the presence of nitrogen oxides or nitric acid. The oxidation with oxygen in the presence of nitric acid is described, for example, in U.S. Pat. Nos. 2,697,722 and 2,727,920.

These publications relate to the oxidation of alkylmercaptans or polysulfides (such as dialkyl disulfides) with oxygen absorbed in nitric acid. The alkylmercaptan or the polysulfide is oxidized in stages to give the desired alkanesulfonic acid. During the oxidation, mixtures of nitrogen monoxide, nitrogen dioxide and nitrous oxide form. The nitrogen monoxide and the nitrogen dioxide are converted by the oxygen absorbed in the nitric acid into pure nitrogen dioxide or into nitric acid, which in turn are available for the formation of alkanesulfonic acids. The nitrous oxide is excluded from the system. A disadvantage of this process is the high content of nitrous oxide formed which, as a "greenhouse gas" similar to halogenated methanes and ethanes, leads to ecological problems and must therefore be separated off from the offgas stream in an industrial plant, which is a complex procedure. Furthermore, the offgases also comprise relatively large amounts of nitrogen and sulfur compounds, which likewise must be removed in a complex procedure.

The reaction temperatures for these reactions are usually in the range between 25 and 70° C. However, at these temperatures complete conversion to the alkanesulfonic acid is not achieved. Thus, for example, in the reaction to give methanesulfonic acid, under these reaction conditions the reaction partially remains at the stage of the intermediate product S-methyl methanethiosulfonate. This intermediate is an unstable compound which releases sulfur dioxide from 90° C. and decomposes spontaneously and extremely exothermally at 170° C.

It is therefore an object of the present invention to provide an economically attractive process which permits the preparation of alkanesulfonic acids in high purity and in good yields, and suppresses virtually completely the formation of nitrous oxide.

This object is achieved by a process for the preparation of alkanesulfonic acids, comprising the following steps:

(a) oxidation of alkylmercaptans and/or dialkyl disulfides and/or dialkyl polysulfides having from three to nine sulfur atoms with nitric acid to form alkanesulfonic acids, water, nitrogen oxides and other byproducts, (b) regeneration of the nitrogen oxides obtained from step (a) with oxygen to give nitric acid and recycling of the nitric acid to step (a).

The process according to the invention comprises carrying out the steps (a) and (b) in reaction chambers separate from one another.

Accordingly, the net reaction carried out is an oxidation of the alkylmercaptan or of the dialkyl disulfide with (atmospheric) oxygen.

The nitrogen oxides which form in step (a) are low oxidation state nitrogen compounds ($NO/NO_2$ mixtures), which are reoxidized in step (b) to give pure nitric acid or nitric acid containing nitrogen dioxide. The nitric acid used in the process according to the invention can, accordingly, be pure nitric acid or nitric acid containing nitrogen dioxide.

The spatial separation of the oxidation of mercaptans and/or dialkyl disulfides and/or dialkyl polysulfides having from three to nine sulfur atoms to give alkanesulfonic acid (step (a)) and the regeneration of the nitrogen oxides (step (b)) is advantageous because both reaction steps, step (a) and step (b), can be carried out separately from another another under optimal reaction conditions. As a result, the formation of nitrous oxide can be suppressed virtually completely, and it is possible to achieve very good yields of alkanesulfonic acids.

The process according to the invention is preferably carried out continuously.

Step (a)

The oxidation is usually carried out at elevated temperature in order to obtain a high conversion and in order to avoid a buildup of hazardous trace components such as methyl nitrate or S-methyl methanethiosulfate as can form during the preparation of methanesulfonic acid. In general, step (a) is carried out at reaction temperatures of from 50° C. to 150° C., preferably from 100° C. to 140° C. The operating pressure in step (a) is generally between 100 mbar and 8 bar, preferably atmospheric pressure.

The mercaptans and/or dialkyl disulfides and/or dialkyl polysulfides used in the process according to the invention contain hydrocarbons which can be aliphatic or cycloaliphatic. Particularly preferably, the hydrocarbon radicals are linear or branched aliphatic hydrocarbon radicals. These preferably contain from 1 to 20, particularly preferably from 1 to 14, carbon atoms. Very particularly preferably, the radicals are methyl radicals and thus the alkylmercaptans or dialkyl disulfides are methylmercaptan or dimethyl disulfide.

Preference is given to using dialkyl disulfides in the process according to the invention. The dialkyl disulfides are generally prepared from hydrogen sulfide and methanol, although other access methods are also known in the literature. Particularly preferably the dialkyl disulfides are prepared by oxidation of alkylmercaptans with sulfur dissolved in an organic dialkyl disulfide using an amine as catalyst. In this process the alkylmercaptans can be used as "crude mercaptan stream", i.e. as mercaptan stream not purified by extraction or distillation, from the reaction of alcohols with hydrogen sulfide on a suitable catalyst.

An advantage of this preparation process for dialkyl disulfides is that the process can be carried out at atmospheric pressure. This means that dialkyl disulfide which is stored temporarily is not kept in a pressurized container. In addition, dialkyl disulfide is a storage-stable feed material and can therefore be handled safely. This process is described in patent application Ser. No. 198 54 427.8 (official file reference) which has been filed at the same time and has the title "Process for the preparation of dialkyl disulfides".

The dialkyl disulfide which is preferably used is reacted to give alkanesulfonic acid and must therefore be replenished. Replenishment of dialkyl disulfides can take place into the vapor phase of the reaction mixture in step (a) or immersed below the surface of the liquid of the reaction mixture. If the addition is into the vapor phase of the reaction mixture, intimate mixtures of dialkyl disulfides and nitrogen oxides can form, which are explosive. The dialkyl disulfides are therefore preferably metered into the reaction mixture immersed under the surface of the liquid. Immersion can, for example, take place in the reactor via an immersion tube or in a circulation circuit via a mixing nozzle.

The molar ration of alkylmercaptans and/or dialkyl disulfides and/or dialkyl polysulfides having from three to nine sulfur atoms to nitric acid is, for mercaptan, generally from 1:1 to 1:10, preferably from 1:2 to 1:6, particularly preferably from 1:2 to 1:4. For dialkyl disulfides, the molar ratio is generally from 1:2 to 1:20, preferably from 1:3 to 1:10, particularly preferably from 1:3 to 1:6.

The dialkyl polysulfides are preferably used in a mixture with mercaptans or dialkyl disulfides.

The oxidation can be carried out in one reactor or in a battery of reactors with a high degree of back-mixing, e.g. in a stirred-tank reactor or loop reactor, or in a reactor with a low degree of back-mixing, e.g. in a tubular flow reactor. Preference is given to carrying out step (a) in one reactor or in a battery of reactors with a high degree of back-mixing. If reactors or batteries of reactors with a high degree of back-mixing are used, then these can, if desired, be operated below the boiling point of the reaction mixture as pure oxidation reactors, or at the boiling point of the reaction mixture, where, during the synthesis, concentration of the reaction mixture can be achieved simply by removing excess dilute aqueous nitric acid.

In a preferred embodiment, the oxidation part of the plant consists of a battery of two reactors with a high degree of back-mixing, e.g. two stirred-tank reactors. The temperature in the first reactor, into which alkylmercaptan or dialkyl disulfide and nitric acid are metered, is preferably between 50 and 140° C., particularly preferably between 80 and 120° C. The second reactor, which is charged with the overflow from the first reactor, is preferably operated between 100 and 150° C., particularly preferably between 130 and 150° C. with evaporation of the reactor contents. The residence times of the reaction mixture in the two reactors can be between 10 minutes and 10 hours, preferably between 1 and 3 hours.

Some of the heat of the reaction of the oxidation of the mercaptan or dialkyl disulfide is preferably dissipated via a condenser placed in the offgas stream with condensate recycle to the reaction mixture.

If step (a) is carried out in a battery of two reactors with a high degree of back-mixing, then the alkylmercaptan or dialkyl disulfide or dialkyl polysulfide used is largely oxidized in the first reactor, where essentially the corresponding alkane sulfonic acid and, in a small amount, incomplete oxidation products as well as excess nitric acid and small amounts of sulfuric acid form. The yield of alkane sulfonic acid in the mixture is, at this stage of the reaction, usually already greater than 80%, preferably than 90%, based on the amount of mercaptan and/or dialkyl disulfide and/or dialkyl polysulfide used. In the second reactor completion of the oxidation reaction takes place, as a result of which the yield of alkanesulfonic acid is usually increased to more than 90%, preferably more than 93%.

The excess nitric acid present in the discharge from reaction step (a) can be separated off distillatively by simple distillation in a manner known per se using water and be recycled to the oxidation of mercaptans and/or dialkyl disulfides and/or dialkyl polysulfides (step (a)) or to the regeneration of the nitrogen oxides with oxygen to give nitric acid (step (b)). The other byproducts which form in the reaction discharge from step (a) can also be separated from one another distillatively, the products of incomplete oxidation preferably being returned to the oxidation (step a)).

In this manner, virtually all of the nitric acid is retained in the system, the only losses occurring due to the formation of very small amounts of nitrous oxide and incomplete absorption in step (b). The absorption losses are, however, only small according to the current position of modern nitric acid plants.

In a preferred embodiment, the second reactor is attached to a water separation column operated as a stripping column. This separates off water and nitric acid as top product, and the bottom product typically obtained is a colorless 98% strength alkanesulfonic acid containing approximately 1% by weight of water and approximately 1% by weight of sulfuric acid. Nitric acid is only present in traces of <0.2% by weight. The column is generally operated at from 20 to 1000 mbar, preferably from 50 to 300 mbar and at still temperatures of generally from 130 to 240° C., preferably from 150 to 200° C.

Step (b)

The regeneration of the nitrogen oxides ($NO/NO_2$ mixtures) is generally carried out at low temperatures and increased pressures in order to achieve very good absorption of the regenerated nitrogen oxides $NO_x$ and thus to obtain a very highly concentrated nitric acid.

For the purposes of the present invention, $NO_x$ is essentially taken to mean NO, $NO_2$, $N_2O_3$, $N_2O_4$ and $N_2O_5$.

The concentration of the nitric acid used in the process according to the invention is generally from 20 to 100% by weight, preferably from 40 to 70% by weight, particularly preferably from 50 to 70% by weight. Preference is given to carrying out step (b) isothermally at temperatures of from 0° C. to 60° C., particularly preferably from 0° C. to 30° C. The absolute pressures are preferably between 0.5 and 20 bar, particularly preferably between 3 and 12 bar.

The regeneration of the nitrogen oxides in step (b) is effective at the same time as offgas washing for the sulfur compounds produced in step (a) as byproducts, meaning that the process offgas is free from malodorous mercaptans or dialkyl disulfides or dialkyl polysulfides, and approximately corresponds in its composition to that of current nitric acid plants. The offgas can therefore be released into the surroundings without additional post-treatment.

The oxygen used for the regeneration is generally atmospheric oxygen.

The reaction apparatus used is generally an absorption column. It is preferably a cooled absorption column which corresponds to known columns for the preparation of nitric acid from nitrogen oxides. These can, for example, be boiling, valve, bubble-cap, tunnel-cap columns or columns packed with dumped or arranged packing. Cooling can take place either in the column or in external heat exchangers.

The absorption column is generally operated at from 0 to 60° C., preferably from 0 to 30° C., preferably isothermally. Fresh water, preferably demineralized water, is added at the top of the column, where lean air (i.e. air depleted in oxygen) largely freed from nitrogen oxide escapes.

In the process according to the invention for the preparation of alkanesulfonic acids, the nitric acid present in the reaction discharge in step (a) is, accordingly, preferably returned, following removal from the reaction discharge, to step (a) or step (b), and the products of incomplete oxidation which are likewise present are, after removal, returned to step (a).

The already very pure alkanesulfonic acid obtained in the process according to the invention can be purified in a downstream vacuum distillation column, which generally operates at head pressures of from 0.1 to 20 mbar, preferably from 2 to 10 mbar. In this case, impurities which occur in traces are separated off at the top or at the bottom of the column. The actual alkanesulfonic acid is usually obtained in a sidestream takeoff. The resulting alkanesulfonic acid is colorless and generally has a purity of >99%, preferably of >99.5% with a sulfuric acid content of >50 ppm. Methanesulfonic acid obtained in this way is suitable, for example, for use in electrochemical baths.

Very particularly preferably, methanesulfonic acid is prepared in the process according to the invention by oxidation of dimethyl disulfide. The methanesulfonic acid obtained after purification (vacuum distillation) generally has a purity of >99% and is colorless. The sulfuric acid contents are generally less than 50 ppm. Such a methanesulfonic acid is particularly suitable for use in electrochemical baths.

In the accompanying drawings, FIG. 1 shows diagrammatically the process according to the invention. Here, R1 is reactor 1 in which step (a) is carried out
R2 is reactor 2 in which step (b) is carried out
RSH/R—S—S—R is mercaptan used and/or dialkyl disulfide used
$HNO_3$ is nitric acid used
r-$HNO_3$ is nitric acid recycled from step (b) into step (a)
NO/$NO_2$ are low oxidation state nitrogen compounds (NO/$NO_2$ mixtures)
$H_2O$ is water
"$O_2$" is atmospheric oxygen
X is offgas
P is the reaction discharge, comprising the reaction product The example below additionally illustrates the invention.

EXAMPLE

Experimental Set-up

Figure 2:
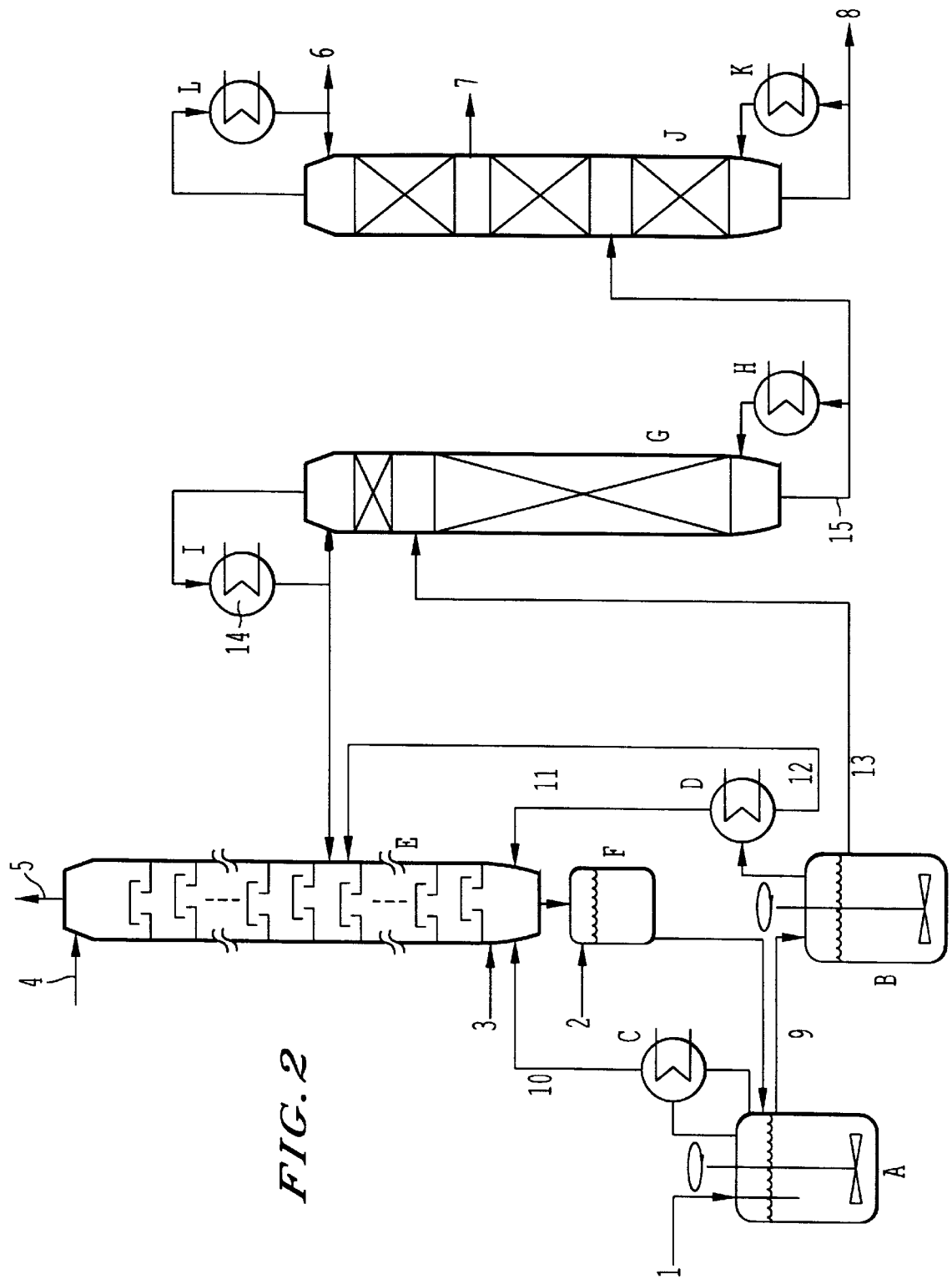

The attached plant diagram (FIG. 2) shows the experimental set-up.

Apparatus

A $1^{st}$ oxidation reactor (stirred-tank reactor)
B $2^{nd}$ oxidation reactor (stirred-tank reactor)
C Condenser
D Condenser
E Plate column containing 44 bubble-cap plates for the regeneration of nitric acid
F Buffer container for nitric acid
G $1^{st}$ vacuum rectification column with glass ring packing
H Bottom product heat exchanger
I Condenser with reflux divider
J $2^{nd}$ vacuum rectification column with arranged packing
K Bottom product heat exchanger
L Condenser with reflux divider Streams 1 Feed of pure dimethyl disulfide
2 Nitric acid feed
3 Air feed
4 Feed of deionized water
5 Exhaust air
6 Low-boiling component outflow
7 Methanesulfonic acid outflow
8 High-boiling components outflow
9 Outflow from the first to the second oxidation reactor
10 Offgas from the first oxidation reactor
11 Offgas from the second oxidation reactor
12 Condensate stream from the second oxidation reactor to the nitric acid regeneration
13 Outflow from the second oxidation reactor to the first vacuum rectification column
14 Condensate stream from the first vacuum rectification column for the nitric acid regeneration
15 Bottom product discharge from the first to the second vacuum rectification column Experimental Details The reactor A is charged continuously, with stirring, via 1 with pure dimethyl disulfide (>98%) and from F with 45 to 50% strength nitric acid in the DMDS (dimethyldisulfide): $HNO_3$ molar ratio of 1:5. The dimethyldisulfide is introduced beneath the surface. The temperature in the reactor A is 100° C. The residence time in reactor A, calculated as a quotient of the liquid volume in reactor A, divided by the liquid stream 9 which is continuously leaving reactor A, is about 2.2 h.

The liquid stream 9 which is continuously leaving reactor A consists of about 32% of methanesulfonic acid, 11% of nitric acid, 0.6% of S-methyl methanethiosulfonate and 56% of water and is fed to reactor B. The temperature in reactor B is 130° C. The residence time in reactor B, calculated as a quotient of the liquid volume in reactor B, divided by the liquid stream 13 which is continuously leaving reactor B, is about 2.2 h. The liquid stream 13 which is continuously leaving reactor B consists of about 55% of methanesulfonic acid, 10% of nitric acid, <0.2% of S-methyl methanethiosulfonate and 35% of water and is passed to the vacuum rectification column G just below the top of the column. The crude yield of methanesulfonic acid in stream 9 is >95%.

The vacuum rectification column G operates at a head pressure of from 95 to 100 mbar (absolute) and a still temperature of 180 to 190° C.

The bottom product 15 leaving the vacuum rectification column G consists of about 98% of methanesulfonic acid, about 1% of water and about 1% of sulfuric acid and is fed to vacuum rectification column J.

Vacuum rectification column J operates at a head pressure of from about 5 to 10 mbar (absolute) and a still temperature of from about 180 to 190° C.

The side take-off stream 7 leaving the vacuum rectification column J consists of >99% strength methanesulfonic acid having a sulfuric acid content of <50 ppm. The total yield of methanesulfonic acid after distillation is >90%.

The head take-off stream 6 leaving the vacuum ectification column J consists of water, methanesulfonic acid, methyl methanesulfonate and other low-boiling components. The bottom product take-off stream 8 leaving the vacuum rectification column J consists of sulfuric acid, methanesulfonic acid and other high-boiling components.

The plate column for the nitric acid regeneration E operates at normal pressure and at temperatures of 20 to 45° C.

The ionized water is fed via feed 4 to the plate column for the regeneration of nitric acid E.

The air introduced into the plate column for the regeneration of nitric acid E via stream 3 for the reoxidation of the nitrogen oxides leaves the column at the top exit 5 with a reduced oxygen content (7 to 13% by volume).

The $NO_x$-containing offgas stream 10 formed in reactor A and freed from condensable components in condenser C comprises NO and $NO_2$ and is passed to the plate column for the regeneration of nitric acid E.

The $NO_x$-containing offgas stream 11 formed in reactor B and freed from condensable components in condenser D comprises NO and $NO_2$ and is passed to the plate column for the regeneration of nitric acid E.

The condensate 12 consists of about 7% strength nitric acid and is passed to the plate column for the regeneration of nitric acid E to a plate having a similar plate concentration of nitric acid.

The condensate 14 consists of about 23% strength nitric acid and is fed to the plate column for the regeneration of nitric acid E to a plate having a similar plate concentration of nitric acid.

The bottom product outflow from the plate column for the regeneration of nitric acid E to the nitric acid buffer container F consists of about 45 to 50% strength nitric acid and is fed to the reactor A.

Nitric acid losses are replaced by topping up the required amounts of 50 to 65% strength nitric acid via stream 2 into the nitric acid buffer container F.

We claim:

1. A process for the preparation of alkanesulfonic acids, comprising the following steps:

(a) oxidation of alkylmercaptans and/or dialkyl disulfides and/or dialkyl polysulfides having from three to nine sulfur atoms with nitric acid to form alkanesulfonic acids, water, nitrogen oxides and other byproducts, (b) regeneration of the nitrogen oxides obtained from step (a) with oxygen to give nitric acid and recycling of the nitric acid to step (a), which comprises carrying out steps (a) and (b) in reaction chambers separate from one another.

2. A process as claimed in claim 1, wherein the process is carried out continuously.

3. A process as claimed in claim 1, wherein step (a) is carried out at reaction temperatures of from 50 to 150° C. and at an operating pressure of from 100 mbar to 8 bar.

4. A process as claimed in claim 1, wherein the alkyl mercaptans or the dialkyl disulfides or the dialkyl polysulfides contain hydrocarbon radicals having from 1 to 20 carbon atoms.

5. A process as claimed in claim 1, wherein dialkyl disulfides are oxidized in step (a).

6. A process as claimed in claim 5, wherein dimethyl disulfide is oxidized.

7. A process as claimed in claim 1, wherein some of the heat of the reaction of the oxidation of the mercaptan or of the dialkyl disulfide or of the dialkyl polysulfide is dissipated by a condenser placed in the offgas stream with condensate recycling.

8. A process as claimed in claim 1, wherein step (b) is carried out at from 0 to 60° C. and at an operating pressure of from 0.5 to 20 bar.

9. A process as claimed in claim 1, wherein step (b) is carried out in a cooled absorption column.

10. A process as claimed in claim 1, wherein the nitric acid present in the reaction discharge in step (a) is, after having been removed from the reaction mixture, returned to step (a) or step (b), and the products of incomplete oxidation which are likewise present are, after they have been removed, returned to step (a), and the alkanesulfonic acid is separated off.

* * * * *